United States Patent [19]

Khoury

[11] Patent Number: 5,217,454
[45] Date of Patent: Jun. 8, 1993

[54] LASER DELIVERY CATHETER
[75] Inventor: Adib I. Khoury, Bellows Falls, Vt.
[73] Assignee: Angiolaz, Incorporated, Bellows Falls, Vt.
[21] Appl. No.: 739,321
[22] Filed: Aug. 1, 1991
[51] Int. Cl.$^5$ .............................. A61B 17/36
[52] U.S. Cl. ........................... 606/7; 606/14; 606/15; 606/16
[58] Field of Search ............ 606/14, 15, 17, 4, 170, 606/13; 604/95; 128/4, 6

[56] References Cited

U.S. PATENT DOCUMENTS

| | | |
|---|---|---|
| 4,418,688 | 12/1983 | Loeb . |
| 4,445,892 | 5/1984 | Hussein et al. ............ 606/7 |
| 4,669,467 | 6/1987 | Willett et al. . |
| 4,820,264 | 4/1989 | Matsui et al. ............ 606/4 |
| 4,832,023 | 5/1989 | Murphy-Chutorian et al. . |
| 4,844,062 | 7/1989 | Wells . |
| 4,848,336 | 7/1989 | Fox et al. . |
| 4,850,351 | 7/1989 | Herman et al. . |
| 4,854,315 | 8/1989 | Stack et al. . |
| 4,860,743 | 8/1989 | Abela . |
| 4,862,886 | 9/1989 | Clarke et al. . |
| 4,875,897 | 10/1989 | Lee . |
| 4,878,492 | 11/1989 | Sinofsky et al. . |
| 4,878,725 | 11/1989 | Hessel et al. . |
| 4,887,605 | 12/1989 | Angelsen et al. . |
| 4,913,142 | 4/1990 | Kittrell et al. . |
| 4,917,084 | 4/1990 | Sinofsky . |
| 4,976,688 | 12/1990 | Rosenblum ............ 604/95 |
| 5,041,108 | 8/1991 | Fox et al. ............ 606/7 |

Primary Examiner—Stephen C. Pellegrino
Attorney, Agent, or Firm—Donald S. Holland

[57] ABSTRACT

An apparatus and method are disclosed for transmitting laser energy to occlusions within obstructed vessels. In the preferred embodiments, a laser delivery catheter includes a hollow tip that encloses a laser energy optical fiber and retractable endoscope. In use, the hollow tip is first positioned adjacent an occlusion. The endoscope can then be retracted within the hollow tip to enhance utilization of the internal volume of the hollow tip for positioning of the laser energy optical fiber, thereby allowing targeting of the occlusion substantially beyond a cross-sectional area of the hollow tip. In a "balloon" embodiment, the position of the laser energy optical fiber is adjusted by an inflatable balloon, adjacent the optical fiber, within the hollow tip. In a "wire" embodiment, the position of the optical fiber is adjusted by a longitudinal movement of a torque wire.

8 Claims, 3 Drawing Sheets

LASER DELIVERY CATHETER

BACKGROUND OF THE INVENTION

The present invention relates to medical catheter design and use, and more particularly to the design of catheters utilizing laser-light energy for removal of blood vessel occlusions.

More than four million Americans suffer yearly from some form of arteriosclerotic coronary artery disease according to American Heart Association estimates. Arteriosclerosis, or obstruction of blood vessels with consequent interruption of blood flow, results from deposits of "plaque" within blood vessels' hollow lumina. Plaque consists of calcium, fibrous tissue, and fatty substances. It is categorized according to its calcium content. "Soft", recently-deposited, plaque contains small amounts of calcium, while "hard" or aged plaque contains proportionately greater amounts of calcium.

Efforts to find new procedures for improving blood flow through obstructed blood vessels have so far taken two directions. One technique is balloon angioplasty, also known as the "Grüntzig" balloon catheter technique. In this non-operative procedure, a "Grüntzig" catheter is delivered into an obstructed coronary artery. An inflatable balloon on the catheter tip is expanded at the site of obstruction or stenosis. Inflation of the balloon compresses plaque that forms the obstruction, widens the blood vessel lumen, and so improves blood flow. Balloon angioplasty works well on about 5% of all arteriosclerotic patients. The procedure works best when used to treat "soft" plaque obstructions in unconstricted arteries.

"Hard" plaque does not respond well to treatment by balloon angioplasty and necessitates more rigorous treatment procedures such as bypass surgery or endarterectomy. Surgical treatment for arteriosclerosis is associated with high morbidity and mortality rates, however, as well as tremendous costs and lengthy hospitalizations. Unfortunately, patients may suffer arterial spasms, embolization, thrombal occlusion and perforated blood vessels by use of this procedure.

A second approach to improving blood flow within obstructed vessels is that of laser vaporization. Continuous-wave laser energy delivered by flexible means to an obstructed site can effectively vaporize hard plaque and reopen a lumen to blood flow.

However, serious safety risks and laser-targeting problems accompany the use of laser vaporization in blood vessels. The amount of laser energy needed to vaporize hard plaque is also sufficient to vaporize healthy tissues. A primary difficulty, then, is the possible perforation of a vessel wall when a laser beam is targeted at an occlusion affixed to the wall. Especially risky and life-threatening is the treatment of coronary artery blockages by use of laser vaporization. In addition, since laser energy damages tissues by thermal necrosis or degradation, possible thermal damage may occur in tissues surrounding an occluded area.

Attempts to avoid such hazards and still allow use of the laser vaporization technique have resulted in a variety of designs for laser energy delivery systems. Flexible catheters having multiple internal channels emerged as a preferred means for this purpose. Channels within such catheters may carry an endoscope or guidewire, provide conduits for visualization media, gas injection, laser energy transmission, and/or suctionning tubes for debris removal. A catheter's degree of flexibility limits its usefulness for reaching obstructions within tortuously curved blood vessels and for permitting appropriate targeting of laser energy to effect vaporization.

In addition to multiple channels, a number of catheter designs disclose extensive use of inflatable balloons. Some balloons are placed external to the catheter and, when inflated, form a collar to secure the position of the catheter within a blood vessel and to prevent blood flow beyond the catheter. Other designs, as disclosed in U.S. Pat. No. 4,875,897 to Lee and U.S. Pat. No. 4,848,336 to Fox, include inflatable balloons within the catheter adjacent a distal end of the catheter that is positioned next to an obstruction in a vessel. Selective inflation of these internal balloons move optical fibers that transmit laser energy and permit appropriate targeting of the obstruction.

Control wires or cables provide an alternative method to internal positioning balloons for optical fiber movement. As shown in U.S. Pat. No. 4,913,142 to Kittrell et al., U.S. Pat. No. 4,669,467 to Willett et al., and U.S. Pat. No. 4,418,688 to Loeb, control wires may be affixed at or near a distal end of an optical fiber. Rotational or longitudinal movement of these wires permits a change in position of the distal end of an optical fiber to effect greater flexibility for targeting of the laser beam transmitted by the optical fiber. Applicant hereby incorporates by reference U.S. Pat. No. 4,669,467 to Willett et al.; U.S. Pat. No. 4,848,336 to Fox; and U.S. Pat. No. 4,913,142 to Kittrell et al.

Flexibility of the laser transmitting optical fiber within the catheter of known designs is severely restricted, however, due to inherent structural limitations. Catheter designs that lack internal positioning balloons or control wires have a targeting capacity limited to obstructions that lie in a straight path before them. Since blood vessels normally follow tightly curved paths, vessel wall perforation is a common problem. Catheter designs that include positioning balloons or control wires afford increased flexibility for targeting obstructions compared to less complicated catheter designs, but are still incapable of completely targeting obstructions located within tight vascular curves that approximate the distal end of the catheter as it is threaded through an obstructed blood vessel. Either catheter design requires an operator to frequently rotate or reposition a catheter within an obstructed blood vessel in order to cover a targeting range that meets or extends beyond a catheter's cross-sectional area. Repeated manipulation by an operator increases the level of operating difficulty and associated safety risks.

Structural limitations exist in presently known catheter designs that restrict handling and use of the catheter. For example, the presence of a number of internal balloons for aiming laser beams restricts the internal space available within a catheter required for related tasks and necessitates a multitude of connections for gas control, supply and escape routes. This, in turn, makes physical handling of the catheter cumbersome for an operator and limits the overall flexibility of the catheter. The same spatial and handling problems are encountered when numerous wires or cables are used for targeting laser beams.

Accordingly, it is the main object of the present invention to provide an improved laser delivery catheter which overcomes the deficiencies of the prior art.

It is another general object to provide an improved laser delivery catheter that consists of fewer components and so is less costly to manufacture.

It is a more specific object to provide a laser delivery catheter for transmission of laser energy that minimizes laser targeting requirements during operation.

It is yet another object to provide a simple laser delivery catheter with increased flexibility in order to reach occlusions located within sinuous blood vessels.

It is still another object to provide a laser delivery catheter that safely allows laser energy targeting beyond a cross-sectional area of the catheter.

It is yet another object to provide a laser delivery catheter with increased flexibility of the laser-delivery optical fiber within the catheter to permit targeting and vaporization of closely-occurring obstructions.

The above and other objects and advantages of this invention will become more readily apparent when the following description is read in conjunction with the accompanying drawings.

SUMMARY OF THE INVENTION

An improved laser delivery catheter is disclosed for transmitting laser energy to obstructed vessels. The laser delivery catheter is affixed to a standard medical laser and endoscope eyepiece.

In a first preferred, or "balloon", embodiment, the invention comprises a flexible catheter having a balloon hollow tip that houses a retractable endoscope, a laser energy optical fiber, and a targeting balloon. In a second preferred, or "wire" embodiment, the targeting balloon is replaced with a torque wire.

In use, the hollow tip of the flexible catheter is positioned adjacent an occlusion in a vessel. The position of the laser energy optical fiber is adjusted to target a proper portion of the occlusion, by the balloon in the first embodiment, or by the torque wire in the second. By retracting the endoscope within the hollow tip, the laser energy optical fiber can be moved throughout the volume defined by the hollow tip. That movement affords targeting of portions of the occlusion substantially beyond a cross-sectional area of the hollow tip.

DETAILED DESCRIPTION OF THE PREFERRED EMBODIMENTS

Figure 1:
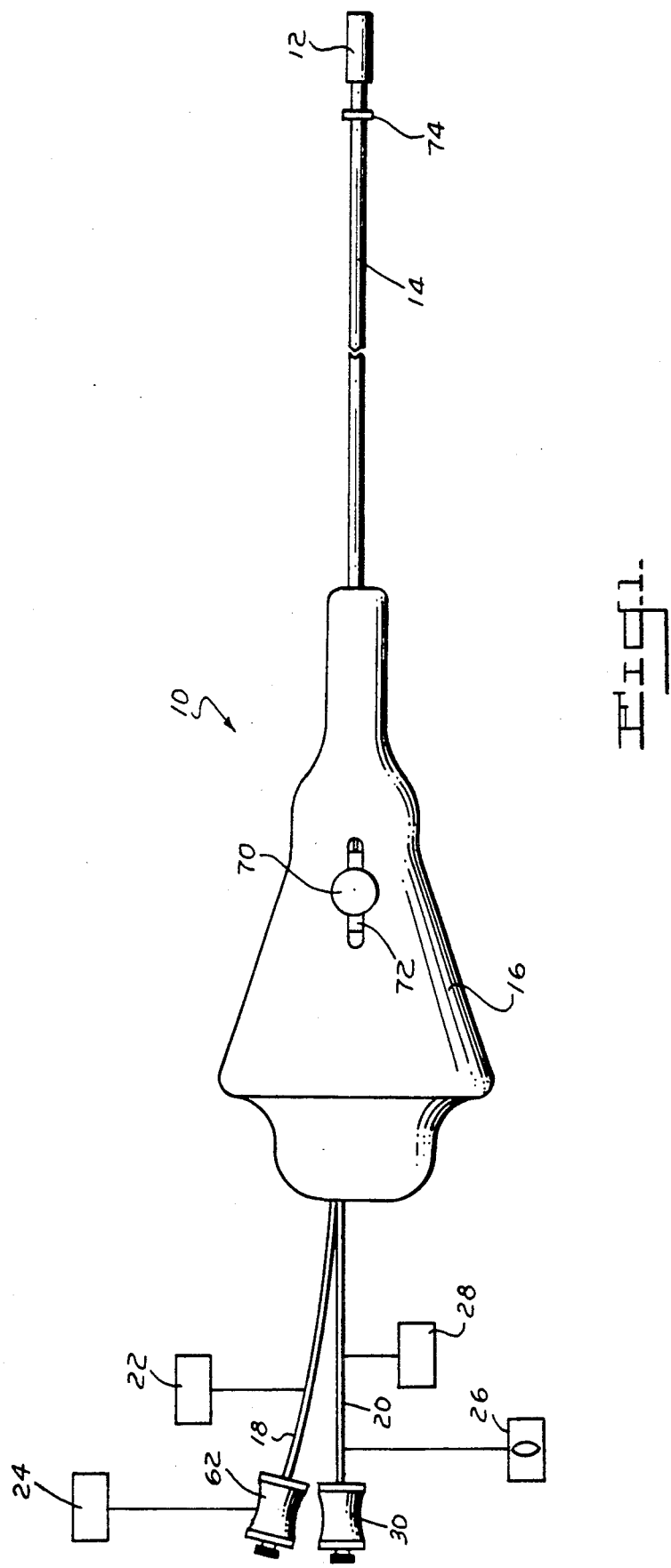
FIG. 1 is a plan view of a laser delivery catheter constructed in accordance with the present invention, wherein the catheter is affixed to a standard medical laser, endoscope eyepiece, and saline solution injector.

Referring to the drawings in detail, a first preferred or balloon embodiment of a laser delivery catheter of the present invention is shown and generally designated by the reference numeral 10. As seen in FIG. 1, the invention basically comprises a balloon hollow tip 12 affixed to a catheter 14 that extends from a catheter handle 16. A laser-adjustment feed 18 and an endoscope-adjustment feed 20 are affixed to the catheter handle 16. A standard medical laser 22, such as HoCrT-H:YAG, Model Nos. LAS 1000G and LAS 1000S, manufactured by Laser Photonics, of 12351 Research Parkway, Orlando, Fla., and a balloon-inflation manipulator 24, such as a thumb bladder, Model No. B001, manufactured by Faultless Rubber, of 268 E. Fourth Street, Ashland, Ohio, are affixed to laser-adjustment feed 18. A standard endoscope eyepiece 26, such as Reusable Ocular, Model No. ANDA 100, manufactured by Vermont Medical, Inc., of Industrial Park, Bellows Falls, Vt., a standard 30 cc syringe saline-solution injector 28 and an endoscope-position manipulator 30, such as Inner Assembly Model No. IA 001, manufactured by AngioLaz, Incorporated, of 10 Transportation Park, Rockingham, Vt., are affixed to endoscope adjustment feed 20. A balloon-inflation tube 31 extends from the balloon-inflation manipulator 24 to the balloon hollow tip 12 (see FIGS. 2, 3).

Figure 2:
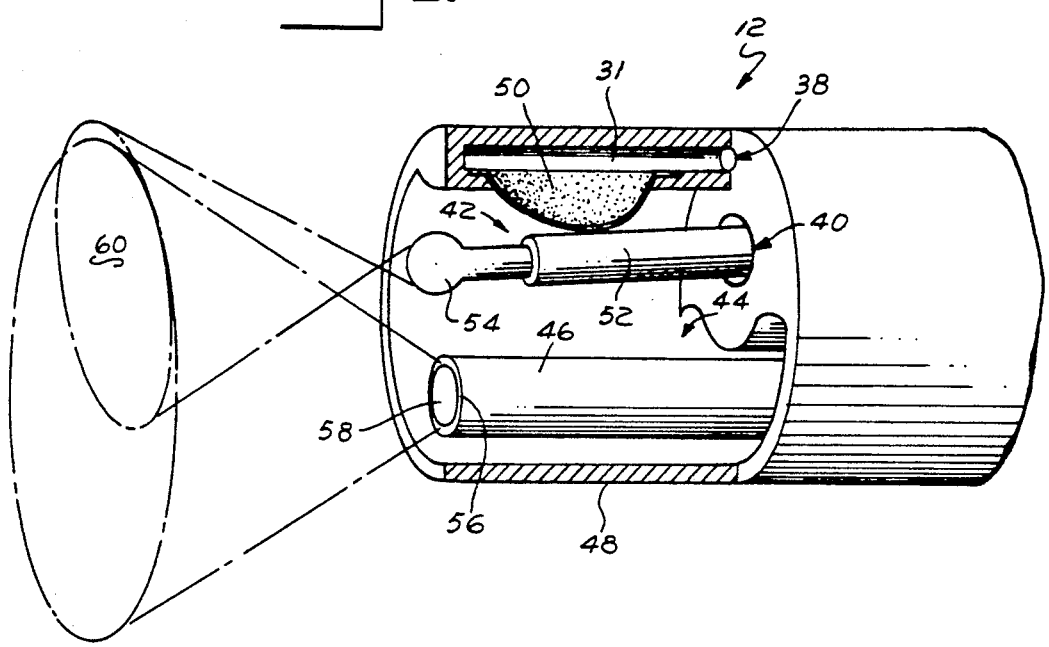
FIG. 2 is a fragmentary perspective view of a hollow tip of a balloon embodiment of the laser delivery catheter of FIG. 1, wherein an endoscope is extended, showing in hatched lines an area viewed through the endoscope, and an area targeted by a laser energy optical fiber.
Figure 3:
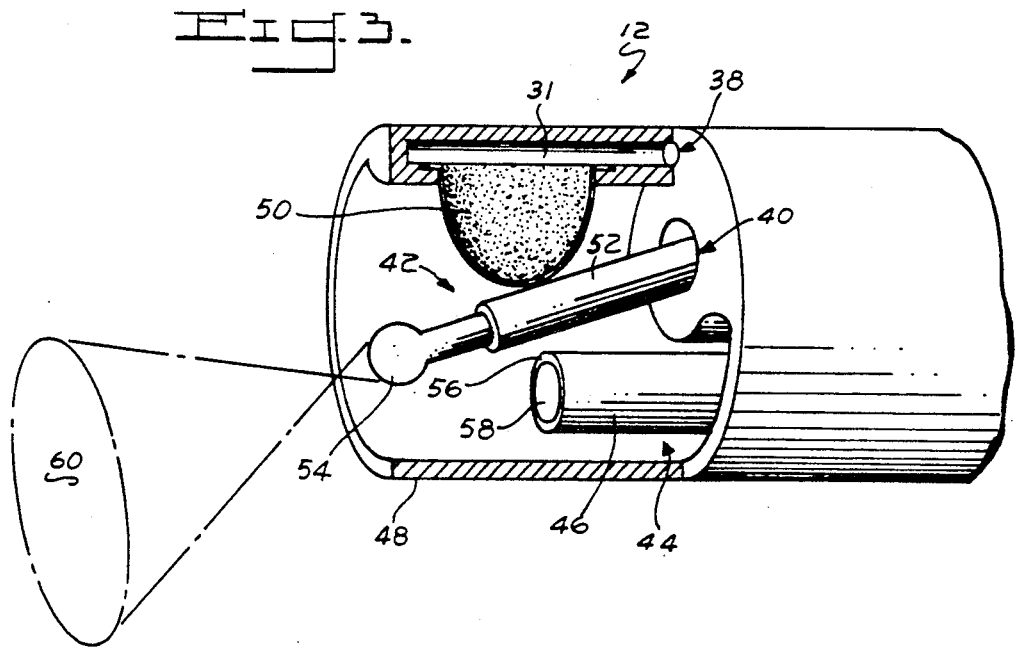
FIG. 3 is a fragmentary perspective view of the hollow tip of FIG. 2, wherein the endoscope is retracted and a targeting balloon is extended to adjust the position of the laser delivery optical fiber, showing in hatched lines an adjusted area targeted by the laser energy optical fiber.

As shown in FIGS. 2 and 3, in the balloon embodiment 10 of the laser delivery catheter, the balloon hollow tip 12 includes a first balloon lumen 38, encasing the balloon-inflation tube 36; a second balloon lumen 40, housing a laser energy optical fiber 42 such as Model No. LOF 001, manufactured by Polymicro Technologies, 3035 North 33rd Drive, Phoenix, Ariz.; and a third balloon lumen 44, housing a retractable endoscope 46, such as Disposable Scope, Model No. ADA 1600, 3000 or 6000, manufactured by Vermont Medical, Inc., of Industrial Park, Bellows Falls, Vt. A balloon cylindrical wall 48 of the balloon hollow tip 32 surrounds laser energy optical fiber 42 and endoscope 46, and is affixed to balloon inflation tube 36. An adjustment balloon 50 extends from the balloon-inflation tube 31 to contact the laser energy optical fiber 42.

Laser energy optical fiber 42 includes an internally reflective and protective cladding 52 and a focusing end lens 54 such as Micro Lens, Model Nos. ML 400 or ML 600, manufactured by AngioLaz, Incorporated, 10 Transportation Park, Rockingham, Vt. Retractable endoscope 46 includes a light emitting collar 56 and an image transmitting object lens 58.

In using the balloon embodiment 10 of the laser delivery catheter, an operator (not shown) positions the balloon hollow tip 12 adjacent a vessel occlusion (not shown) through conventional catheter positioning means. The operator observes in the endoscope eyepiece 26 an image of the occlusion formed by light emitted from the collar 56 of the endoscope 46, reflecting off the occlusion and passing through the object lens 58, and through the endoscope 46 to the eyepiece 26. To enhance visualization of the occlusion, the operator can manipulate the saline solution injector 28 to inject a saline solution through the third balloon lumen 44 into the area adjacent the occlusion.

To properly target the laser energy optical fiber 42, the operator initiates transmission from the medical laser 22 of low energy laser light, of a specific color, through the laser energy optical fiber 42. The low energy laser light is focused by the focusing end lens 54 so that a circle of light 60 having specific color contacts the occlusion, and is viewed by the operator through the endoscope eye piece 26. As shown in FIGS. 2 and 3, the focusing lens 54 acts to create a direct proportion between a distance from the lens 54 to the circle 60 and a length of a diameter of the circle of light 60. The operator adjusts the distance between the focusing lens 54 and the occlusion, by longitudinal movement of the entire laser delivery catheter 10, so that the diameter of the circle matches a pre-determined length. The operator then initiates transmission, by the medical laser 22, of a pulse, or pulses of high energy laser energy through the laser energy optical fiber 42. The amount of laser energy transmitted is pre-determined to vaporize material making up the occlusion only at the distance from the focusing lens 54 determined by the length of the diameter of the circle of light 60. Beyond that distance, the focusing end lens 54 causes the energy to be too diffuse for vaporization, thereby avoiding possible inadvertent damage to a vessel (not shown) containing the occlusion.

The entire laser delivery catheter 10 can be axially rotated, by axial rotation of the catheter handle 16, in order to target and vaporize portions of the occlusion corresponding to a cross-sectional area of the balloon hollow tip 32, adjacent to the tip. To completely remove the occlusion, or to move the balloon hollow tip 32 forward, into and beyond the occlusion, it may be necessary for the operator to target and vaporize a portion of the occlusion beyond a cross-sectional area of the hollow tip 12. In that event, the operator utilizes the endoscope-position manipulator 30 to retract the endoscope 46, as shown in FIG. 3. The operator then utilizes the balloon-inflation manipulator 24 to pass a fluid along the balloon inflating tube 31 and into the adjustment balloon 50. As a result of the increased volume of fluid, the adjustment balloon 50 expands, causing the laser energy optical fiber 42 to move, as seen in FIG. 3. The operator observes the resulting movement of the low energy laser circle of light 60, and stops passing fluid into the adjustment balloon 50, via manipulation of the balloon-inflation manipulator 24, when the circle of light 60 is in the desired position. The operator then repeats the same longitudinal positioning of the balloon hollow tip, to acquire a proper, pre-determined diameter of circle of light 60, and then transmits sufficient high energy laser energy through the laser energy optical fiber 42 to vaporize the occlusion within the circle of light. The operator can repeat the process until the balloon hollow tip removes the occlusion or "mines" a tunnel completely through the occlusion, that is substantially wider than the cross-sectional area of the tip 12.

Figure 4:
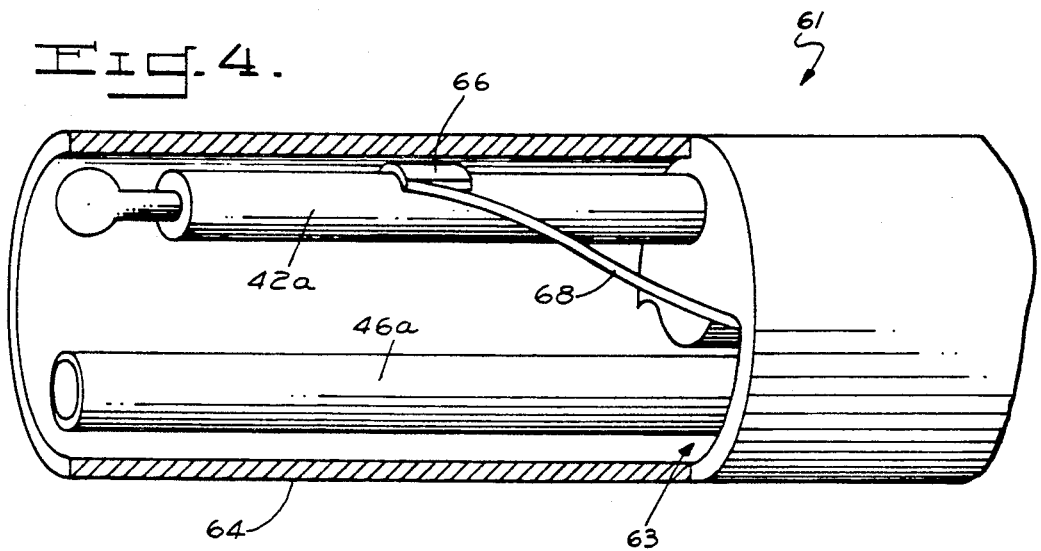
FIG. 4 is a fragmentary perspective view of the hollow tip of a wire embodiment of the laser delivery catheter of FIG. 1, wherein an endoscope is extended.
Figure 5:
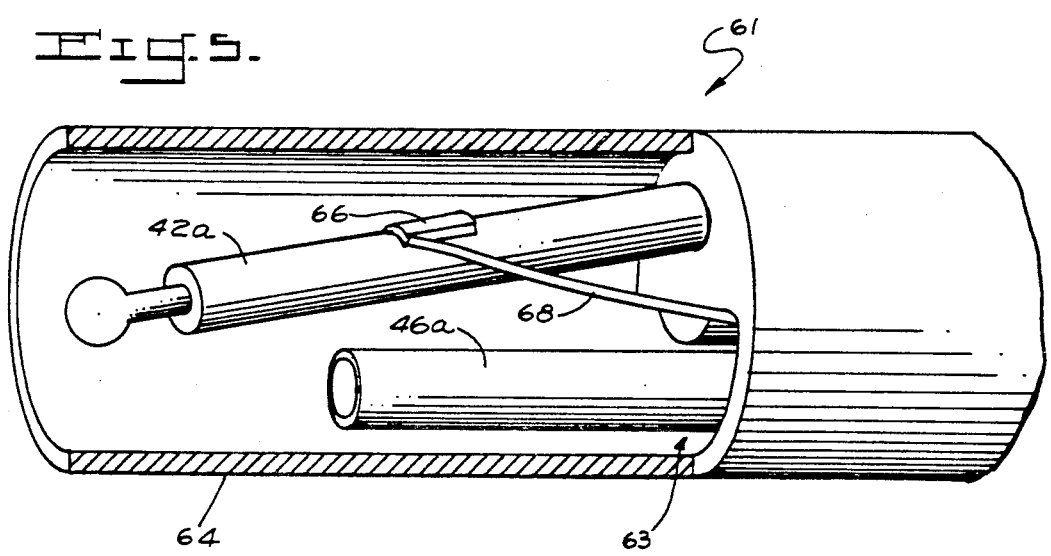
FIG. 5 is a fragmentary perspective view of the hollow tip of FIG. 4, wherein the endoscope is retracted, and a position of a laser energy optical fiber is adjusted by a torque wire.

As shown in FIGS. 1, 4, 5, a second preferred or wire embodiment of the invention is identical to the balloon embodiment 10, except a wire hollow tip 61 (seen in FIGS. 4, 5) replaces the balloon hollow tip 12, and the balloon position manipulator 24 is replaced with a threaded wire position manipulator 62. The wire hollow tip 61, seen in FIGS. 4 and 5, includes a wire lumen 63 housing a retractable endoscope 46a that is identical to the retractable endoscope 46 in the balloon hollow tip 12. A wire cylindrical wall 64 of the wire hollow tip 61 surrounds the retractable endoscope 46a, and a laser energy optical fiber 42a that is identical to the laser energy optical fiber 42 in the balloon hollow tip 12, except a step 66 is affixed to optical fiber 42a. Torque wire 68 is affixed to the step 66 and extends through wire lumen 63, the catheter 12, catheter handle 16, laser adjustment feed 18, to the wire-position manipulator 62, as seen in FIGS. 1, 4 and 5. Catheter handle 16 includes a wire-position securing bolt 70 with a wire access slot 72. Manipulation of the bolt 70 applies pressure to the torque wire 68 to secure the wire in a fixed position.

In using the wire embodiment of the laser delivery catheter, an operator utilizes the same methods (as with the balloon embodiment) for positioning the hollow tip 61; targeting the laser energy optical fiber 42a on portions of an occlusion corresponding to a cross-sectional area of the wire hollow tip 61; and vaporizing those portions. To target and vaporize portions of the occlusion beyond the cross-sectional area of the wire hollow tip 61, the operator utilizes the endoscope-position manipulator 30 to retract endoscope 46a. The operator then utilizes wire-position manipulator 62 to retract the torque wire 68, thereby moving laser energy optical fiber 42a, as shown in FIG. 5. As with the balloon embodiment, the operator observes movement of the low energy laser circle of light 60 (not shown in FIGS. 4, 5; see FIGS. 2, 3). When the circle is in the desired position, the operator secures the torque wire 68 against further movement by manipulation of the wire-position securing bolt 70, in the catheter handle 16. The operator then vaporizes the occlusion within the circle 60, as with the balloon embodiment, and repeats the process until the wire hollow tip 61 removes the occlusion, or "mines" a tunnel completely through the occlusion, that is substantially wider than the cross-sectional area of the tip 61.

Both the balloon and wire embodiments of the laser delivery catheter preferably also include an inflatable collar circumferential balloon 74, which is affixed to the catheter 14, and is of conventional, known design, like the circumferential balloon described in U.S. Pat. No. 4,848,336 to Fox et al. (shown in Fox et al. at FIG. 4, No. 43, and described at Column 9, line 54 -Column 10, line 18), which Patent is hereby incorporated by reference. The collar circumferential balloon 74 is inflated during targeting and vaporization to occlude the vessel between the catheter handle 16 and either the balloon or wire hollow tips 12, 61, thereby enhancing visualization of the occlusion by minimizing dilution of the saline solution by other liquids within the vessel.

It should be understood by those skilled in the art that obvious structural modifications can be made without departing from the spirit of the invention. Accordingly, reference should be made primarily to the accompanying claims rather than the foregoing specification to determine the scope of the invention.

Having thus described the invention, what is claimed is:

1. An apparatus for transmitting laser energy to an occlusion within a vessel, that comprises:
   a. a laser, adapted to adjustably generate laser energy;
   b. a laser energy optical fiber, affixed to the laser so that a first end of the laser energy optical fiber receives laser energy, and an opposed second end of the laser energy optical fiber emits laser energy;
   c. a catheter, adapted to house the laser energy optical fiber so that a first end of the catheter is adjacent the first end of the laser energy optical fiber, and an opposed second end of the catheter positions the second end of the laser energy optical fiber adjacent the occlusion;

d. an endoscope housed within the catheter in parallel association with a longitudinal axis of the laser energy optical fiber, wherein the endoscope includes a light-transmission end that shines visible light on the occlusion and transmits an image reflected off the occlusion back through the endoscope to a viewing end of the endoscope, where an operator of the apparatus views the image;

e. a hollow tip affixed to the second end of the catheter adapted to define a hollow cylindrical cavity surrounding the second end of the laser energy optical fiber and the light-transmission end of the endoscope;

f. a torque wire having a position adjustment end affixed to the second end of the laser energy optical fiber and an opposed manipulation end adjacent the first end of the catheter, said wire also having a longitudinal axis in parallel association with a longitudinal axis of the endoscope;

g. a wire position manipulator affixed to the manipulation end of the torque wire, adapted to selectively move the torque wire along its longitudinal axis causing selective adjustment of the position of the second end of the laser energy optical fiber; and h. a wire position securing bolt, adjustably affixed to the first end of the catheter adjacent the manipulation end of the torque wire, so that adjustment of the wire position securing bolt secures the torque wire in a fixed position.

2. An apparatus for transmitting laser energy to an occlusion within a vessel, that comprises:

a. a laser, adapted to adjustably generate laser energy;

b. a laser energy optical fiber, affixed to the laser so that a first end of the laser energy optical fiber receives laser energy and an opposed second end of the laser energy optical fiber emits laser energy;

c. a catheter, adapted to house the laser energy optical fiber so that a first end of the catheter is adjacent the first end of the laser energy optical fiber and an opposed second end of the catheter positions the second end of the laser energy optical fiber adjacent the occlusion;

d. a retractable endoscope adjustably housed within a lumen in the catheter in parallel association with a longitudinal axis of the laser energy optical fiber, wherein the endoscope includes a light-transmission end that shines visible light on the occlusion and transmits an image reflected off the occlusion back through the endoscope to a viewing end of the endoscope, where an operator of the apparatus views the image, and the retractable endoscope is adapted to adjustably move within the lumen in the catheter along a longitudinal axis of the endoscope so that the light-transmission end of the endoscope adjustably retracts towards the first end of the laser energy optical fiber and away from the second end of the laser energy optical fiber;

e. a hollow tip affixed to the second end of the catheter adapted to define a hollow cylindrical cavity surrounding the second end of the laser energy optical fiber and the light-transmission end of the endoscope; and f. position adjustment means for selectively adjusting a position of the second end of the laser energy optical fiber substantially throughout the cylindrical cavity defined by the hollow tip.

3. The apparatus of claim 2, wherein the position adjustment means comprises:

a. an endoscope position manipulator affixed to the viewing end of the retractable endoscope, and adapted to selectively move the endoscope along its longitudinal axis so that the light transmission end of the endoscope can be withdrawn from a first position within the hollow tip adjacent the second end of the laser energy optical fiber to selected positions within the hollow tip toward the first end of the laser energy optical fiber;

b. an inflatable balloon affixed to the hollow tip adjacent the second end of the laser energy optical fiber;

c. a balloon inflation tube in fluid connection with the inflatable balloon, having a longitudinal axis in parallel association with a longitudinal axis of the catheter; and d. a balloon-inflation manipulator in fluid connection with the balloon inflation tube, and adjacent the first end of the catheter, adapted to selectively pass a fluid through the balloon inflation tube into the inflatable balloon so that the balloon inflates and contacts the second end of the laser energy optical fiber, causing a selective adjustment of the position of the second end of the laser energy optical fiber.

4. The apparatus of claim 2, wherein the light-transmission end of the retractable endoscope includes a light-emitting collar surrounding an image transmitting object lens, adapted to shine visible light from the collar onto the occlusion and transmit an image of the occlusion formed by the object lens through the endoscope to the viewing end of the endoscope.

5. The apparatus of claim 4, wherein the second end of the laser energy optical fiber includes a focusing lens adapted to focus laser energy passing out of the second end of the laser energy optical fiber.

6. An apparatus for transmitting laser energy to an occlusion within a vessel, that comprises:

a. a laser, adapted to adjustably generate laser energy;

b. a laser energy optical fiber, affixed to the laser so that a first end of the laser energy optical fiber receives laser energy and an opposed second end of the laser energy optical fiber emits laser energy;

c. a catheter, adapted to house the laser energy optical fiber so that a first end of the catheter is adjacent the first end of the laser energy optical fiber and an opposed second end of the catheter positions the second end of the laser energy optical fiber adjacent the occlusion;

d. a retractable endoscope adjustably housed within a lumen in the catheter in parallel association with a longitudinal axis of the laser energy optical fiber, wherein the endoscope includes a light-transmission end that shines visible light on the occlusion and transmits an image reflected off the occlusion back through the endoscope to a viewing end of the endoscope, where an operator of the apparatus views the image, and the retractable endoscope is adapted to adjustably move within the lumen in the catheter along a longitudinal axis of the endoscope so that the light-transmission end of the endoscope adjustably retracts towards the first end of the laser energy optical fiber and away from the second end of the laser energy optical fiber;

e. a hollow tip affixed to the second end of the catheter adapted to define a hollow cylindrical cavity surrounding the second end of the laser energy optical fiber and the light-transmission end of the endoscope;

f. an endoscope position manipulator affixed to the viewing end of the retractable endoscope, and adapted to selectively move the endoscope along its longitudinal axis so that the light transmission end of the endoscope can be withdrawn from a first position within the hollow tip adjacent the second end of the laser energy optical fiber to selected positions within the hollow tip toward the first end of the laser energy optical fiber;

g. a torque wire having a position adjustment end affixed to the second end of the laser energy optical fiber and an opposed manipulation end adjacent the first end of the catheter, said wire also having a longitudinal axis in parallel association with a longitudinal axis of the endoscope; and h. a wire position manipulator affixed to the manipulation end of the torque wire, adapted to selectively move the torque wire along its longitudinal axis causing selective adjustment of the position of the second end of the laser energy optical fiber.

7. The apparatus of claim 6, further comprising a wire position securing bolt, adjustably affixed to the first end of the catheter adjacent the manipulation end of the torque wire, so that adjustment of the wire position securing bolt secures the wire in a fixed position.

8. A method of transmitting laser energy to an occlusion within a vessel, which comprises:

a. positioning a hollow tip of a laser delivery catheter adjacent the occlusion;

b. viewing the occlusion through a light-transmission end of an endoscope within the hollow tip;

c. retracting the light-transmission end of the endoscope within the hollow tip;

d. targeting the occlusion with a laser energy optical fiber within the hollow tip on the occlusion;

e. selectively adjusting the position of the laser energy optical fiber within the hollow tip by selectively adjusting a longitudinal position of a torque wire affixed to, and in substantially parallel alignment with, the optical fiber, thereby adjusting the position of the optical fiber within the hollow tip; and f. transmitting laser energy through the laser energy optical fiber onto the occlusion.

* * * * *